US009770159B2

(12) United States Patent
Gorini

(10) Patent No.: US 9,770,159 B2
(45) Date of Patent: Sep. 26, 2017

(54) FLEXIBLE AND EXTENSIBLE TUBULAR GUIDE AND MANUFACTURE PROCESS THEREOF

(71) Applicant: ERA ENDOSCOPY S.R.L., Peccioli (Pisa) (IT)

(72) Inventor: Samuele Gorini, Montecalvoli (IT)

(73) Assignee: ERA ENDOSCOPY S.R.L., Peccioli (Pisa) (IT)

( * ) Notice: Subject to any disclaimer, the term of this patent is extended or adjusted under 35 U.S.C. 154(b) by 31 days.

(21) Appl. No.: 14/434,087

(22) PCT Filed: Oct. 24, 2013

(86) PCT No.: PCT/IB2013/059613
§ 371 (c)(1),
(2) Date: Apr. 7, 2015

(87) PCT Pub. No.: WO2014/064638
PCT Pub. Date: May 1, 2014

(65) Prior Publication Data
US 2015/0265141 A1 Sep. 24, 2015

(30) Foreign Application Priority Data

Oct. 25, 2012 (IT) .............................. FI2012A0226

(51) Int. Cl.
*A61B 1/005* (2006.01)
*A61B 1/00* (2006.01)
(Continued)

(52) U.S. Cl.
CPC ........ *A61B 1/00154* (2013.01); *A61B 1/0011* (2013.01); *A61B 1/0016* (2013.01);
(Continued)

(58) Field of Classification Search
CPC ............ A61B 1/00073; A61B 1/00075; A61B 1/0011; A61B 1/0016; A61B 1/018; A61B 10/04; A61B 17/00234
(Continued)

(56) References Cited

U.S. PATENT DOCUMENTS 3,648,895 A * 3/1972 Strazdins ............... B65D 35/04
138/119
3,682,202 A * 8/1972 Buhrmann ............... D04B 1/14
138/126

(Continued)

FOREIGN PATENT DOCUMENTS

EP 0838200 4/1998
EP 1792561 6/2007
(Continued)

OTHER PUBLICATIONS

International Search Report mailed on Feb. 17, 2014 for PCT/IB2013/059613 filed on Oct. 24, 2013 in the name of ERA Endoscopy S.R.L.
(Continued)

*Primary Examiner* — John P Leubecker
*Assistant Examiner* — Rajaa El Alami
(74) *Attorney, Agent, or Firm* — Steinfl + Bruno LLP

(57) ABSTRACT

A tubular guide suitable for use as an operating channel for the passage of surgical instruments in an inch-worm-type locomoted endoscopic instrument is described. The guide is fixed to the ends of the central body of the endoscopic instrument and has an elastic and corrugated intermediate portion so as to follow the elongations and the contractions of the central body of the endoscopic instrument without creating an obstacle to the passage of instruments.

15 Claims, 6 Drawing Sheets

(51) Int. Cl.
  *A61B 1/018* (2006.01)
  *A61B 10/04* (2006.01)
  *A61B 17/00* (2006.01)
(52) U.S. Cl.
  CPC ...... *A61B 1/00073* (2013.01); *A61B 1/00075* (2013.01); *A61B 1/018* (2013.01); *A61B 10/04* (2013.01); *A61B 17/00234* (2013.01); *Y10T 29/49908* (2015.01)
(58) Field of Classification Search
  USPC .............................. 138/118, 119, 121, 123
  See application file for complete search history.

(56) References Cited

U.S. PATENT DOCUMENTS

| | | | | | |
|---|---|---|---|---|---|
| 3,779,308 | A | * | 12/1973 | Buhrmann | D04B 1/14 138/125 |
| 4,923,268 | A | * | 5/1990 | Xu | B29C 65/68 264/1.25 |
| 5,108,372 | A | * | 4/1992 | Swenson | A61M 5/16886 604/113 |
| 5,195,976 | A | * | 3/1993 | Swenson | A61M 5/16886 604/113 |
| 5,385,562 | A | * | 1/1995 | Adams | A61M 25/01 604/159 |
| 5,398,670 | A | | 3/1995 | Ortiz et al. | |
| 5,527,292 | A | * | 6/1996 | Adams | A61M 25/0102 600/585 |
| 5,607,407 | A | * | 3/1997 | Tolkoff | A61M 25/005 604/523 |
| 5,662,587 | A | | 9/1997 | Grundfest et al. | |
| 5,665,064 | A | * | 9/1997 | Bodicky | A61J 15/0069 600/156 |
| 5,690,613 | A | * | 11/1997 | Verbeek | A61M 25/0021 604/103 |
| 5,743,891 | A | * | 4/1998 | Tolkoff | A61M 5/3273 604/164.01 |
| 5,792,124 | A | * | 8/1998 | Horrigan | A61M 25/001 604/265 |
| 5,800,487 | A | * | 9/1998 | Mikus | A61B 18/02 606/20 |
| 5,833,825 | A | * | 11/1998 | Otten | G01N 27/301 204/415 |
| 5,906,591 | A | | 5/1999 | Dario et al. | |
| 5,911,715 | A | * | 6/1999 | Berg | A61M 25/0009 138/125 |
| 5,924,289 | A | * | 7/1999 | Bishop, II | F25B 21/04 62/3.61 |
| 5,925,834 | A | * | 7/1999 | Sgourakes | B01L 3/0217 73/864.11 |
| 6,036,682 | A | * | 3/2000 | Lange | A61M 25/0108 604/264 |
| 6,162,337 | A | * | 12/2000 | Iwamoto | G01N 27/4035 156/281 |
| 6,478,606 | B1 | * | 11/2002 | McNerney | H01R 4/22 174/87 |
| 6,505,629 | B1 | * | 1/2003 | Mikus | A61B 18/02 128/898 |
| 6,554,820 | B1 | * | 4/2003 | Wendlandt | A61M 25/005 604/527 |
| 7,048,819 | B1 | * | 5/2006 | Henson | B29C 35/045 156/381 |
| 2001/0049491 | A1 | * | 12/2001 | Shimada | A61M 25/0147 604/95.04 |
| 2003/0102360 | A1 | * | 6/2003 | Eungard | A61M 25/09 228/224 |
| 2003/0109861 | A1 | * | 6/2003 | Shimada | A61M 25/0147 606/14 |
| 2003/0191491 | A1 | * | 10/2003 | Duane | A61M 25/09041 606/194 |
| 2004/0006280 | A1 | * | 1/2004 | Geddes | A61B 5/042 600/509 |
| 2004/0039372 | A1 | * | 2/2004 | Carmody | A61M 25/0113 604/528 |
| 2004/0176833 | A1 | * | 9/2004 | Pavcnik | A61F 2/07 623/1.13 |
| 2004/0220549 | A1 | * | 11/2004 | Dittman | A61M 25/0012 604/526 |
| 2004/0243102 | A1 | * | 12/2004 | Berg | A61M 25/0013 604/525 |
| 2005/0125003 | A1 | * | 6/2005 | Pinchuk | A61F 9/00781 606/108 |
| 2005/0191708 | A1 | * | 9/2005 | Saul | C12N 11/00 435/7.1 |
| 2006/0095050 | A1 | * | 5/2006 | Hartley | A61F 2/95 606/108 |
| 2006/0142704 | A1 | * | 6/2006 | Lentz | A61F 2/95 604/264 |
| 2006/0197420 | A1 | * | 9/2006 | Huang | H01J 61/0672 313/6 |
| 2007/0016185 | A1 | * | 1/2007 | Tullis | A61B 18/1477 606/41 |
| 2007/0043399 | A1 | * | 2/2007 | Stevenson | H05K 9/0039 607/37 |
| 2007/0270679 | A1 | * | 11/2007 | Nguyen | A61M 25/0043 600/373 |
| 2008/0064989 | A1 | * | 3/2008 | Chen | A61M 25/09 600/585 |
| 2008/0141987 | A1 | * | 6/2008 | Skinner | H01F 3/06 123/634 |
| 2008/0157617 | A1 | * | 7/2008 | Hishida | F16C 17/107 310/90 |
| 2008/0167646 | A1 | * | 7/2008 | Godara | A61B 18/1477 606/41 |
| 2008/0234796 | A1 | * | 9/2008 | Dorn | A61F 2/966 623/1.11 |
| 2008/0287786 | A1 | * | 11/2008 | Lentz | A61F 2/95 600/435 |
| 2009/0030284 | A1 | * | 1/2009 | Cole | A61B 1/00078 600/206 |
| 2010/0256445 | A1 | | 10/2010 | Fitzpatrick | |
| 2010/0268264 | A1 | * | 10/2010 | Bonnette | A61B 17/221 606/200 |
| 2011/0172520 | A1 | * | 7/2011 | Lentz | A61F 2/95 600/424 |
| 2011/0295234 | A1 | * | 12/2011 | Eaton | A61M 25/001 604/528 |
| 2012/0010490 | A1 | * | 1/2012 | Kauphusman | A61B 5/0538 600/373 |
| 2012/0035525 | A1 | * | 2/2012 | Silvestrini | A61F 9/00781 604/8 |
| 2012/0130217 | A1 | * | 5/2012 | Kauphusman | A61B 5/0422 600/373 |
| 2012/0130218 | A1 | * | 5/2012 | Kauphusman | A61B 5/0422 600/373 |
| 2012/0172857 | A1 | * | 7/2012 | Harrison | A61B 18/1477 606/33 |

FOREIGN PATENT DOCUMENTS

| | | |
|---|---|---|
| JP | 2000-354633 A | 12/2000 |
| JP | 2001104240 A | 4/2001 |
| WO | 90/07298 | 7/1990 |
| WO | 01/54565 | 8/2001 |
| WO | 02/068035 | 9/2002 |

OTHER PUBLICATIONS

Written Opinion mailed on Feb. 17, 2014 for PCT/IB2013/059613 filed on Oct. 24, 2013 in the name of ERA Endoscopy S.R.L.
Office Action for Japanese Patent Application No. 2015-538613 filed on Oct. 24, 2013 in the name of ERA Endoscopy S.R.L. dated Apr. 20, 2017. 7 pages. Japanese Original + English Translation.

\* cited by examiner

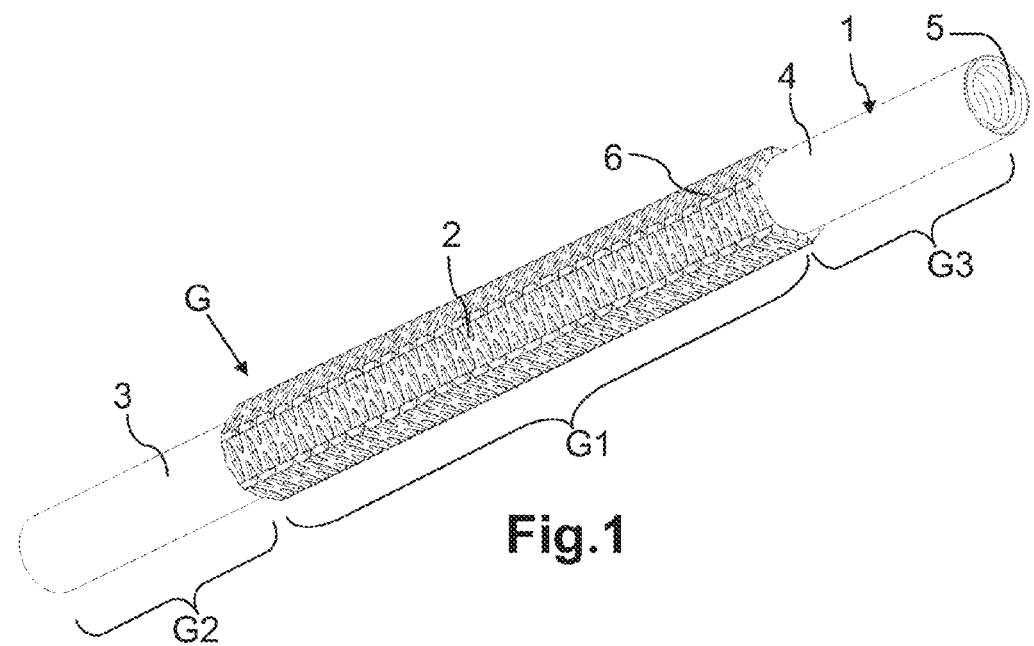
Fig.1
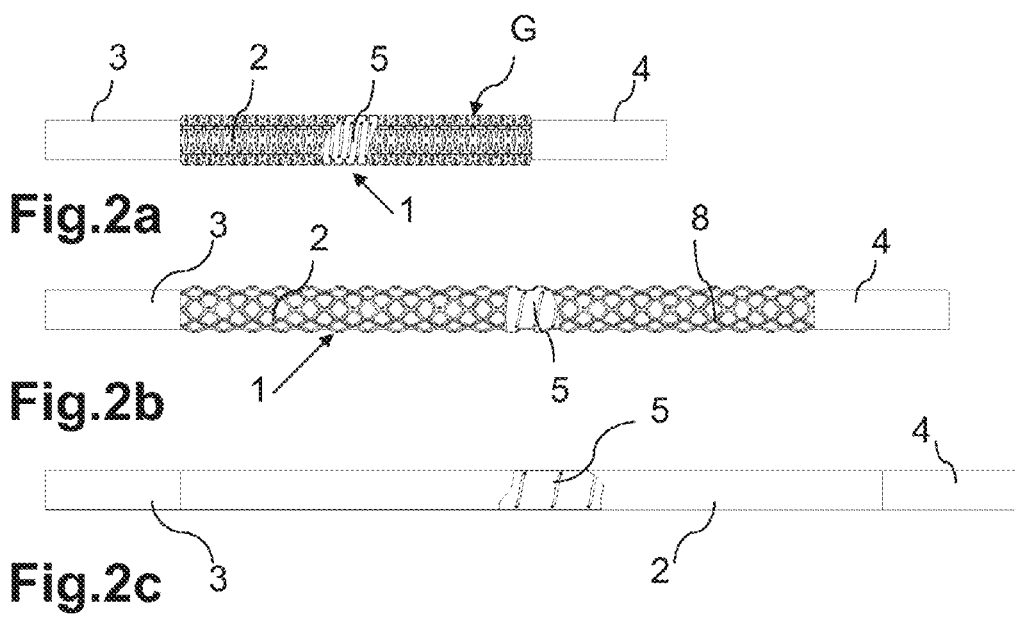
Fig.2a
Fig.2b
Fig.2c

FLEXIBLE AND EXTENSIBLE TUBULAR GUIDE AND MANUFACTURE PROCESS THEREOF

CROSS REFERENCE TO RELATED APPLICATIONS

The present application is the U.S. national stage of International Patent Application PCT/IB2013/059613 filed internationally on Oct. 24, 2013 which, in turn, claims priority to Italian Patent Application No. FI2012A000226 filed on Oct. 25, 2012.

FIELD OF THE INVENTION

The present invention refers to a flexible and extensible tubular guide that can be used in particular, but not exclusively, in equipment and instruments for endoscopy. The invention moreover concerns a process for the manufacture of said tubular guide.

STATE OF THE ART

Endoscopic devices are known for surgical or diagnostic type operations which are actuated by the surgeon who directly controls the movement of the instrument through the body of the patient. Generally, surgical and/or diagnostic instruments that are necessary each time for the specific operations, like micro-arms, micro-cameras and/or laser emitters are associated to the devices.

Endoscopic instruments are also known that are suitable for the locomotion in a tubular body cavity, in particular, but not exclusively, in the gastrointestinal tract, and that are capable of moving in a prefixed advancing direction with a so-called inch-worm type movement.

Endoscopic instruments of this type provided with the ability to move autonomously or semi-autonomously inside the body cavity of a patient are described for example in U.S. Pat. No. 5,398,670, U.S. Pat. No. 5,906,591 and WO02/068035.The endoscopic instrument described in these documents is substantially formed by a tubular central body with a variable length and two end sections, called front and back sections, comprising securing means that make it possible to temporarily and alternatively fix the front end section and the rear end section to the wall of the body cavity so as to allow the instrument to advance. It is worth noting that here and in the rest of the present description the terms "front" and "back" and the like refer to the advancing direction of the endoscopic instrument inside the body area to be inspected.

In particular, the central tubular body of the endoscopic instrument with variable length described in the documents mentioned above takes up the form of a bellows-shaped tubular body, therefore capable of elongating and contracting following introduction of air inside it and sucking of air from it, respectively. In the mentioned patent application PCT n. WO02/068035 the securing of the device to the wall of the body cavity is obtained through clamping means that are associated with the front end and the rear end of the instrument that can be selectively actuated by an external control unit that is synchronised with the successive extensions and contractions of the bellows-shaped tubular body. The aforementioned clamping means are actuated by means of pneumatic actuators that, in the preferred embodiment, also consist of bellow-shaped elements.

During the elongation step, the bellows is pressurised by means of compressed air obtaining an elongation that is proportional to the pressure introduced, whereas in order to obtain the shortening of the bellows, the pressure inside it is progressively reduced until a certain vacuum degree is obtained.

EP1792561 describes one improved version of the endoscopic instrument according to WO02/068035. According to this document, the central tubular body having variable length does not have a bellows configuration, but is flat and made in elastic material and incorporates a reinforcement structure that is arranged along it and is substantially rigid in its radial direction and yieldable in its axial direction, in particular formed by a plurality of rigid rings or by at least one coil spring.

All endoscopic instruments with inch-worm-type locomotion only have diagnostic functions, i.e. they can only transmit images of the body areas through which they transit. Indeed, due to the particular locomotion method of the device, which foresees a succession of elongating and shortening movements of the central body, it is not possible to use a biopsy operating channel of the conventional type for the passage of the surgical instruments, due to the fact that it is inextensible. In conventional endoscopes the biopsy channel is practically a tube that is reinforced in the flexible end part so as to prevent folds from forming when the distal part of the endoscope folds. In order for the central body of the endoscope to be able to elongate and shorten during the locomotion it is thus necessary for the biopsy channel, in the portion inside the endoscope, to elongate and shorten together with the central body.

In order to solve the drawback of the extensible operating channel, inspiration could be taken from patent EP0838200, in which a plastic tube wound in a spiral shape allows the passage of air to a channel at the top of the endoscope. The spiral shape allows the central body to freely elongate and shorten.

In the aforementioned patent the spiral-shaped tube is used to suck/blow air/water inside the intestine. Such a solution however cannot be applied to the embodiment of a biopsy operating channel since it would be necessary for there to be modifications which would not allow it to be used functionally as a biopsy channel. Firstly, in order to house an operating channel of 3 mm, it is necessary for the tube wound in a spiral to have a diameter that is greater than 3 mm (for example 4 mm). Considering that the inner diameter of the central body of the endoscopic instrument is short (currently 12 mm), the resulting spiral would have such an excessive curvature that kinks would be formed, i.e. folds, during the elongation of the central body. Secondly, the surgical instrument would not be capable of advancing through the spiral until it was completely stretched out due to the friction caused by the considerable curvature thereof. The only operative configuration possible would thus be that of a central body that is completely extended so as to "straighten" the spiral. Also in this case there would still be a residual undulation of the tube which would increase the friction in an unacceptable manner. It is moreover worth noting that the strong curvature means that the spiral is considerably rigid (considered like a spring), and such a rigidity would be incompatible with the movement of the central body, since it would counteract its elongation deforming it.

The use of a conventional bellow with a spring inside it, as illustrated in U.S. Pat. No. 5,662,587, could be a good solution for obtaining an extensible operating channel. Indeed the presence of the spring prevents "kinking" and the rectilinear configuration allows the instrument to pass inside it easily.

The difficulties relative to this solution are of the manufacturing type. Manufacturing a bellows with a high L/D ratio (length over diameter), in particular 60 when the central body is in the resting configuration, 120 when the central body is elongated, is difficult, especially in the moulding process. Moreover, there is the difficulty of inserting the spring and the need to have a wall thickness that is sufficiently thin so that the bellows does not become excessively rigid to both bending and in the direction of extension jeopardising its correct operation.

Ultimately, an operating channel for the passage of surgical instruments suitable for being incorporated in an endoscopic instrument of the aforementioned type must have the following characteristics:

1. A diameter that is sufficient to allow biopsy forceps of 2.8 mm, or other surgical instrument with dimensions that are similar (therefore with a channel of at least 3 mm) to pass;
2. The capability of extending by at least twice its initial length, so as to completely follow the stroke of the central body of the endoscope;
3. Flexibility. The endoscope is very flexible and it is necessary for the biopsy channel, to be mounted inside it, to be just as flexible;
4. Low elastic modulus. It is necessary for the biopsy channel to not give strong resistance to the extension in order for the endoscope to not become deformed when its central body extends. Indeed, if the operating channel is too rigid in the direction of extension, there is a bending instability and the endoscope, instead of extending straight, extends forming an "S". This results in the fact that the central body of the endoscope must be considerably more rigid with respect to the operating channel;
5. Strength. The channel must be capable of withstanding the stress generated by the passage of the instrument without becoming damaged;
6. Reduced friction. The channel must allow the passage of the instrument without generating excessive friction;
7. Kink-free. The channel must not form folds or collapse in any configuration;
8. Small bulk. The space inside the central body of the endoscope is small, therefore it is necessary to make an operating channel having small dimensions that can be contained inside it.

SUMMARY OF THE INVENTION

The general purpose of the present invention is to provide a tubular guide that is flexible and extensible, with a diameter in the order of some millimetres, which allows the passage and the sliding of an instrument, such as a surgical instrument, without excessive friction and without interfering with the operation of surrounding components, for example the structure inside which said guide is inserted.

A particular purpose of the present invention is to provide a tubular guide of the aforementioned type that is suitable for being used as an operating channel for the passage of surgical instruments in an endoscopic instrument with inch-worm-type locomotion and capable of following the extension and the contraction thereof without counteracting these movements.

A further purpose of the present invention is to provide a method for producing a flexible and extensible tubular guide of the aforementioned type.

These and further purposes are achieved with the flexible and extensible guide and with the manufacture method thereof according to the present invention, the essential characteristics of which are as defined in claims 1 and 8. Further important characteristics are included in the dependent claims.

An important characteristic of the tubular guide according to the present invention consists of the fact that the tubular member forming it has an intermediate portion that is evenly corrugated in a way such as to allow the guide to extend and contract. Inside the tubular member an elastic element is axially arranged and the tubular member is fixed to the elastic element through two end portions thereof.

In a preferred embodiment of the invention the tubular member is made in heat-shrink material and the evenly corrugated intermediate portion is obtained through plastic deformation thereof, whereas the end portions act as securing means of the tubular member to the internal elastic element following heat-shrinking.

In another embodiment of the invention the tubular member is in plastic material that is fit for being plastically deformed with a plastic range deformation of at least 200%, i.e. following an extension that is equal or greater than 200%, and as means for securing to the internal elastic element it is foreseen for there to be two sleeves in heat-shrink material that following thermal treatment securely fix the end portions of the tubular member to the elastic element.

An important advantage of the tubular guide according to the present invention consists of the fact that, in the case in which it is applied to an endoscope having inch-worm-type locomotion, the doctor is given the possibility of using conventional endoscopy instruments, like for example biopsy forceps, so as to operate in a completely similar way to what he carries out with flexible endoscopes according to the prior art.

BRIEF DESCRIPTION OF THE DRAWINGS

The characteristics and the advantages of the flexible and extensible tubular guide and of the relative production method shall become clearer from the following description of an embodiment thereof given as an example and not for limiting purposes with reference to the attached drawings, in which:

FIG. 1 shows a perspective view of a portion of the tubular guide according to the present invention:

FIG. 2, details a), b) and c), show the tubular guide of FIG. 1 in the resting condition, in the intermediate extension condition and in the complete extension condition;

DETAILED DESCRIPTION OF THE INVENTION

Figure 3:
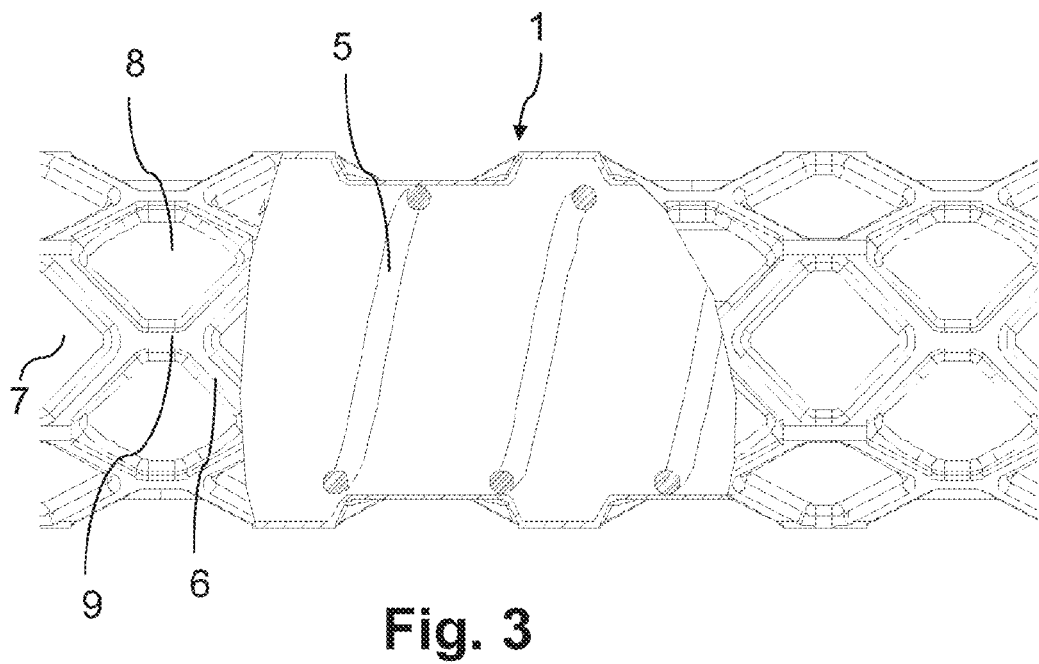
FIG. 3 is a greatly enlarged longitudinal and partially sectioned view of the guide of FIG. 1.

With reference to figures from 1 to 3, reference numeral 1 generally indicates a tubular member of the tubular guide according to the invention indicated as a whole with the letter G. An intermediate portion 2 of the tubular member 1 is evenly corrugated, whereas two end portions 3 and 4 are smooth and are firmly secured to a coil spring 5 that is arranged coaxially inside the tubular member 1. The corrugation of the tubular member 1 at its intermediate portion 2 is formed by a plurality of folds 6 that are interconnected to one another so as to create longitudinal bands or rows 7 of substantially polygonal recesses 8. Each of the bands 7 that extend longitudinally on the intermediate portion 2 of the tubular member 1 is formed by a row of said recesses 8 that are delimited by the folds 6, each of which is connected to the adjacent ones through the respective ends to form knots 9 at the corners of the longitudinal recesses 8.

In the presence of an axial traction or compression stress, the intermediate portion 2 of the tubular member 1 deforms, in particular elongating or shortening correspondingly. FIG. 2 shows how the intermediate portion 2 deforms when there is traction stress. In particular FIG. 2a shows the tubular member 1 in its resting condition with the folds 6 that are very close to one another and the pitch of the spring 5 is very narrow. In this condition, the recesses 8 are almost closed and take up a substantially flattened diamond shape, the knots 9 having a dimension that is substantially point-like. FIG. 2b shows the intermediate extension condition with the folds 6 that are partially stretched out and the spring 5 inside having a greater pitch between its turns. In this condition, due to traction, the recesses 8 widen and for the progressive dilation of the knots 9 they take up a substantially hexagonal shape. FIG. 2c illustrates the condition of maximum extension (at least double): the folds 6 and the knots 9 are completely stretched out and the surface appears to be practically smooth. The spring reaches the maximum designed pitch. A further extension is not possible, because the folds 6 have reached their maximum extension and the intermediate portion 2 of the tubular member 1 cannot extend any further.

When the traction stress is finished the spring 5 contributes towards the contraction of the intermediate portion 2 of the tubular member 1 progressively restoring the surface corrugation.

FIG. 3 shows, in greater detail, the surface corrugation of the intermediate portion 2 in a condition of intermediate extension. Here it can be noted that the progressive extension of the folds 6 due to the extension of the intermediate portion 2 by effect of the axial traction stress exerted on it also causes an elongation of the knots 9 and their consequent extension.

Figure 8:
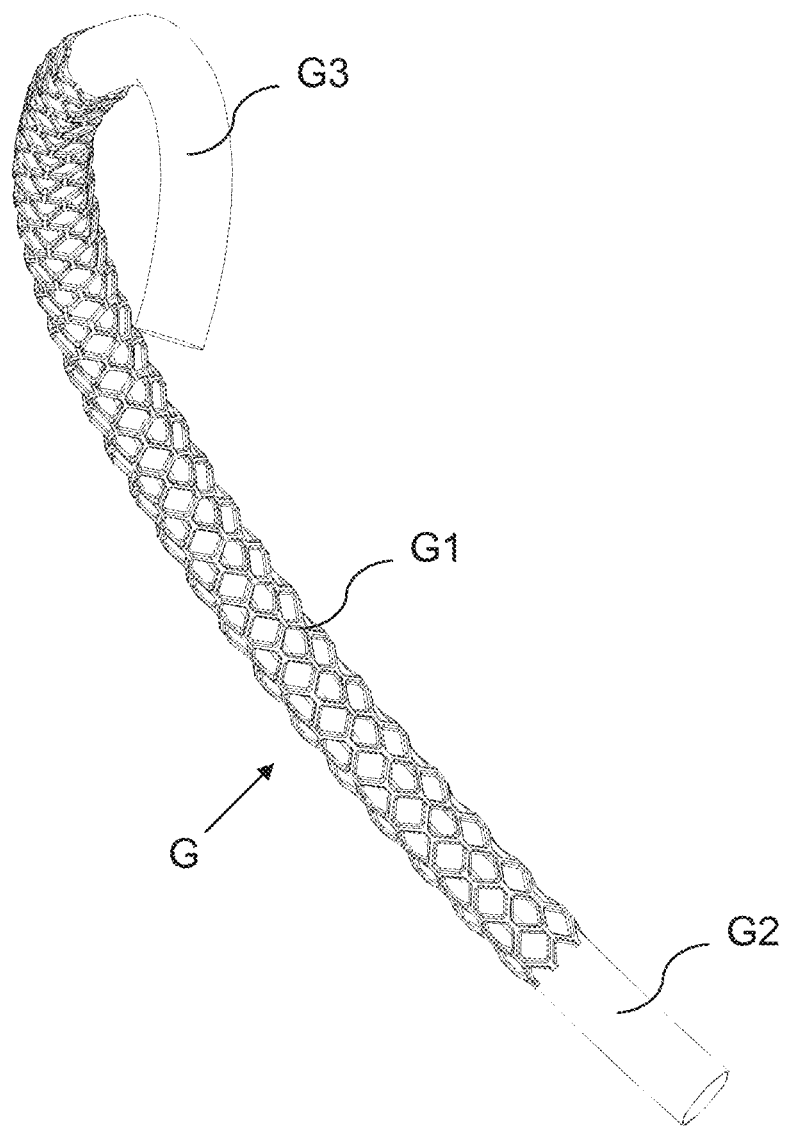
FIG. 8 is a 3D illustration of the tubular guide of FIG. 1 in an intermediate extension condition.

With reference to FIG. 1 and to FIG. 8, the tubular guide G, therefore comprises an extensible portion G1 as a function of the applied axial stress, corresponding to the intermediate portion 2 of the tubular member 1, made extensible thanks to the corrugation present on it, and two inextensible ends, G2 and G3, corresponding to the end portions 3 and 4 of the tubular member 1. Since the end portions 3 and 4 of the tubular member 1, are per se inextensible, firmly connected to the corresponding portions of spring 5, the latter is also inextensible at said portions.

Through the ends G2 and G3 the tubular guide G according to the invention is connected to the ends of the central body of the endoscope (not shown).

Figure 4:
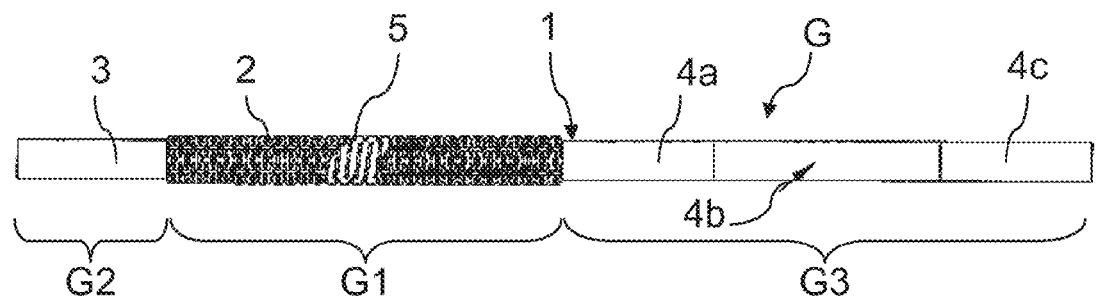
FIG. 4 is a longitudinal view of the tubular guide according to the invention with a flexible end portion so as to allow the endoscope to be steered.

One of the two ends of the tubular guide G, the front end, (in the example the end G3 is illustrated) is predisposed for housing in the part of the endoscopic instrument (steering section) intended to direct the image sensor present in it allowing it to bend by 180° in all directions. For this reason it must be very flexible, but completely inextensible. For such a purpose, as shown in FIG. 4, the front end portion 4 of the tubular member 1 has an inextensible but flexible intermediate part 4b, that is arranged between two rigid and inextensible parts 4a and 4c. The rigid and inextensible part 4a of the front end portion 4 is connected to the end of the central body of the endoscope, whereas the part 4c, also rigid and inextensible, is fixed to the front end of the steering section. The flexible and inextensible part 4b of the tubular member 1 comes out from the front end of the central body of the endoscope and is housed in the steering section. In such a way the end G1 of the tubular guide G can follow without obstructing the movements of the steering section of the endoscope.

The manufacture of the tubular guide according to the invention, in its preferred embodiment, does not foresee the use of moulding systems, but simply implies the plastic deformation of a tube having a thin wall with a spring inside it. The tube is in plastic material that is compatible with the use for which the tubular guide is intended and is suitable for becoming plastically deformed with a plastic range deformation of at least 200%. In the preferred embodiment of the present invention the initial tube is in plastic heat-shrink material. The manufacture process develops according to the following steps.

Figure 5A:
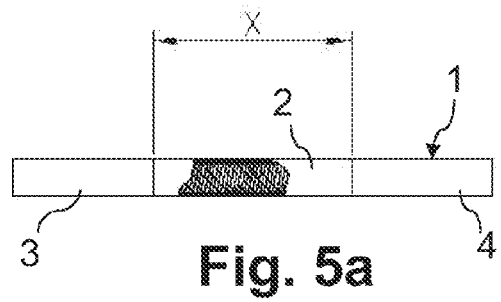
FIG. 5 schematically shows the steps of the production process.
Figure 5B:
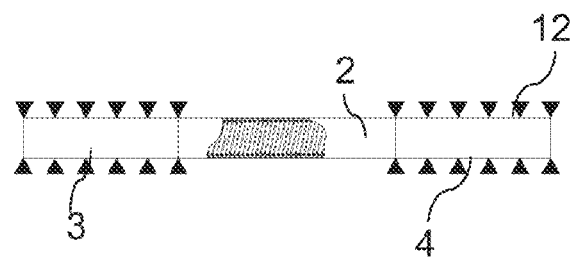

Firstly, a close-wound spring is inserted inside a tube made from plastic heatshrinking material. In the present embodiment the close-wound spring has an outer diameter of 3.6 mm (inner diameter 3 mm) and enters without problems in the plastic heatshrinking tube that has an inner diameter of 3.9 mm. With reference also to FIG. 5, the length of the active portion of the tubular guide being called X, i.e. that intended to be housed inside the central body of the endoscopic instrument having variable length, the portions 3 and 4 are heat-shrunk in a way such as to cause them to perfectly adhere to the underlying spring. In such a way the tube is firmly secured to the proximal and distal end portions of the spring. Following heating, the tube made from plastic has a much smaller diameter and, since the spring prevents the tube from freely retracting, the residual tension firmly keeps the tube stuck to the spring. This makes it possible to firmly fix the tube to the ends of the spring.

Figure 5C:
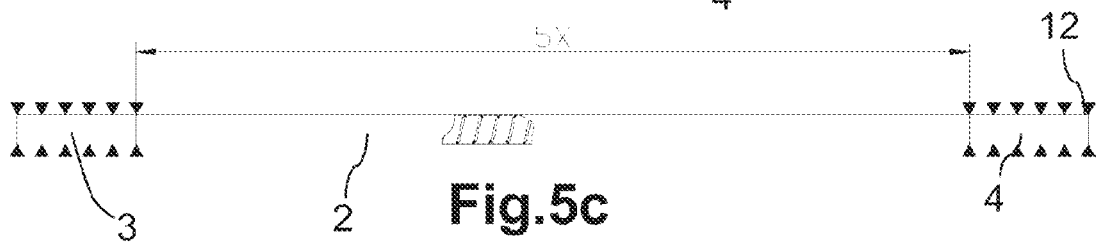
Figure 6:
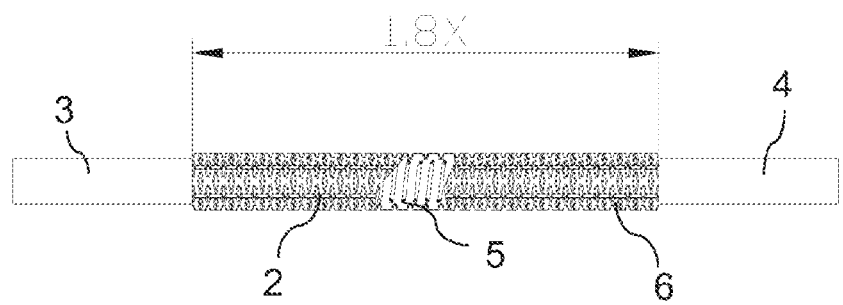
FIG. 6 schematically shows the tubular guide resulting from the production process.

The end portions 3 and 4 (FIG. 5b) are thus firmly blocked by means of suitable constraints, schematically illustrated and indicated with reference numeral 12, and a plastic deformation is imposed on the active portion, having initial length equal to X, so as to extend it by up to five times its length. In practice, an extension is imposed beyond the elastic deformation threshold such as to deform the material of the tubular member in the plastic range within its maximum plastic deformation. In one embodiment the strain at break (δ) of the material is slightly greater than 400%, and indeed it is deformed to a length equal to 5× that corresponds to a deformation of 400% (FIG. 5c). By releasing the constraints 12, the elastic return of the spring brings the length of the active portion of the tubular guide to 1.8× (FIG. 6) at the same time obtaining the folds 6 described above that make it possible to reach the desired performance. The formation of the folds prevents the complete return of the spring to its initial length due to the thickness of the folds themselves.

The heat-shrinking procedure is carried out according to the conventional methods, i.e. through heating of the part to be heat-shrunk by exposing it to hot air. Such an exposure can be carried out with classic air guns or by putting the piece to be heat-shrunk in the oven.

Figure 7A:
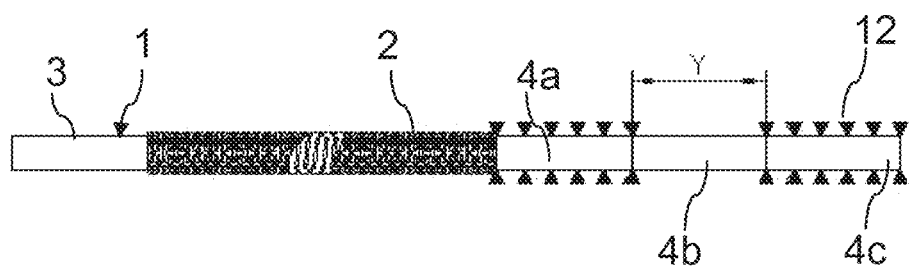
FIG. 7 schematically shows the formation of a length of flexible, but inextensible guide for the steering section of the endoscope.
Figure 7B:
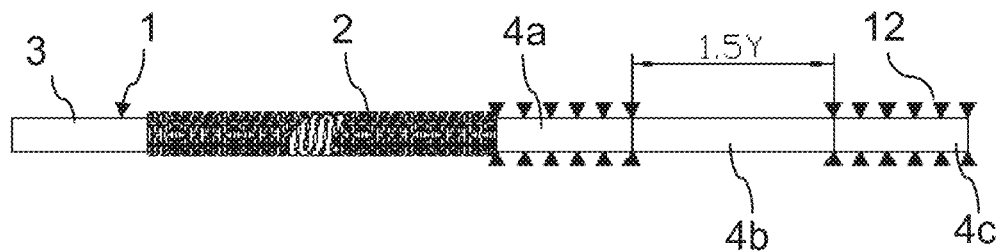
Figure 7C:
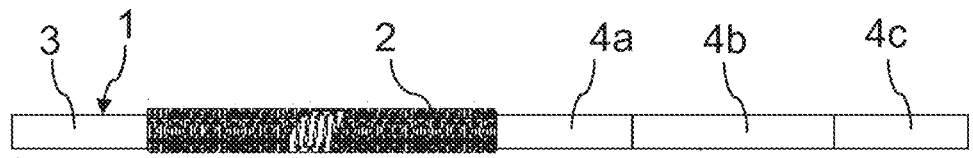

In order to obtain the flexible but inextensible portion 4b of the tubular member 1 intended for the steering section of the endoscopic instrument, the same plastic deformation method described above is used, reducing however the deformation factor to 1.5 (FIG. 7a, b, c) i.e. much lower than the plastic deformation threshold of the material used. The end parts 4a and 4c are then locked (FIG. 7a), there is the plastic deformation of the part between them (FIG. 7b) and the end parts are released (FIG. 7c). In such a way it is possible to obtain the perfect adherence of the tube to the spring without causing folds to form.

If the tube were to simply be heat-shrunk without the moderate elongation set, the portion 4b would be too rigid; if the free space between the spring (Outer diameter 3.6 mm) and the plastic tube (Inner diameter 3.9 mm) were to be left unaltered, the turns could go on top of one another jeopardising the passage of the surgical instrument.

In one example embodiment, the following specifications were used:

Spring

| | |
|---|---|
| Wire diameter | 0.3 mm |
| Average diameter | 3.3 mm |
| Spring-operating channel pitch at rest | 0.5 mm |
| Spring pitch at maximum deformation | 1 mm |

Heat-shrinking plastic tube

| | |
|---|---|
| Internal diameter tube | 3.9 mm |
| Thickness | 0.13 mm |

A heat-shrinking polyolefin tube was used characterised by the strain at break>400% and by tensile strength of between 10 MPa and 20 MPa. Of course, equivalent heat-shrink materials, such as for example PVDF (Polyvinylidene Fluoride), can be alternatively used.

A tubular guide G according to the invention suitable for being used as an operating channel in combination with an endoscope with inch-worm-type locomotion is illustrated in a 3D view in FIG. 8. Here the tubular guide G is shown in its extended condition and with the front end portion 4 intended to be engaged in the steering section of the endoscope markedly folded with respect to the longitudinal axis of the guide so as to highlight the high flexibility of the part 4b thereof.

Figure 9:
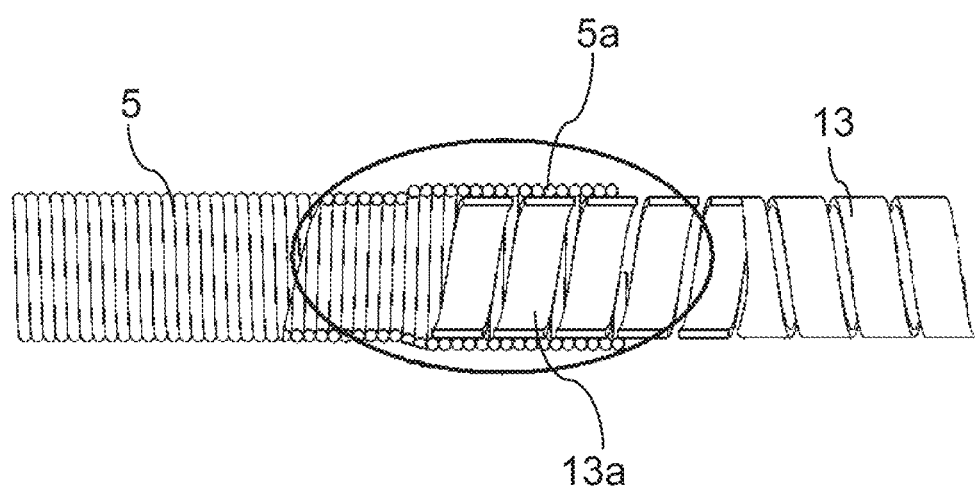
FIG. 9 illustrates a variant embodiment of the front portion of the tubular guide according to the invention.

A variant embodiment of the tubular guide G according to the invention foresees, as shown in FIG. 9, the use of a spring having a wire with a rectangular section, indicated with reference numeral 13, to obtain the end G3 of the guide. More precisely, in this case the spring having rectangular section is engaged in the parts 4b and 4c of the front end portion 4 of the tubular member 1. In the practical embodiment, the spring having circular section 5 has, at one of its ends, a widened section 5a inside which an end 13a of the spring having a rectangular section 13 engages. The process of heat-shrinking the heat-shrink tube arranged above the two springs 5 and 13 engaged with one another follows the modalities that have already been described for the front end portion 4. The two springs 5 and 13 remain fixed to one another following heat-shrinking that is carried out in the connection point between them so as to be rigid and inextensible.

Thanks to the provision described above it is possible to reduce the outer diameter of the front end G3 of the tubular guide G for the same flexural rigidity and the lateral surface of said end is smoother than that which is obtained with the spring with a circular section. This result can be obtained also using a spring with a wire having an elliptical section or in any case generally flattened in the longitudinal direction of the tubular member.

According to another variant embodiment of the invention, the tubular member 1 is made up of a normal tube made from plastic material, for example polyethylene, and at the end portions 3 and 4, it is coupled with respective tube portions, or sleeves, in heat-shrink material tightened around the tube in plastic material. The production process of the tubular guide made with the aforementioned tubular member is the same as that described above and foresees the heat-shrinking of the end portions in heat-shrink material, in such a way obtaining the fixing of the tubular element in plastic material to the spring, and therefore the plastic deformation of the intermediate portion of the tubular member in plastic material. This variant embodiment is not illustrated in greater detail since it is easily understood by a man skilled in the art from what has previously been described.

More in general, glues can be used as means for securing the tubular member in plastic material or the ends of the tubular member and the spring can be over-moulded with a different plastic material.

Concerning the plastic material suitable for being applied in the present invention, in addition to polyethylene, also EVA (Ethylene-vinyl acetate) can be used provided that the plastic range deformation is greater than 200%.

Further variants and/or modifications can be made to the tubular guide according to the present invention and to the relative production method without for this reason departing from the scope of protection of the invention itself as defined in the following claims.

The invention claimed is:

1. A flexible and extensible tubular guide comprising
a tubular member, wherein said tubular member has an intermediate portion which is evenly corrugated in such a way to allow the guide to extend and contract; and
an elastic element axially arranged in said tubular member and internally to the tubular member,
said tubular member being further provided with two end portions fixed to said elastic element,
wherein:
said evenly corrugated intermediate portion of the tubular member comprises a plurality of mutually interconnected folds forming a plurality of elongated diamond recesses when fully axially compressed, and a plurality of hexagonal recesses when fully axially elongated, and
a surface of the tubular member is smoother when the tubular member is fully axially elongated than when the tubular member is fully axially compressed.

2. The tubular guide according to claim 1, wherein said tubular member is made of a deformable plastic material with a plastic range deformation of at least 200% and its end portions are fixed to said elastic element by anchoring means.

3. The tubular guide according to claim 2, wherein said anchoring means comprise two sleeves made of heat shrunk plastic material tightened around said tubular member at the end portions thereof.

4. The tubular guide according to claim 2, wherein said tubular member is made of a heat-shrink material, the intermediate portion thereof being evenly corrugated as a result of plastic deformation, the end portions thereof being heat shrunk to secure themselves to said elastic element.

5. The tubular guide according to claim 1, suitable for the use as operating channel for the passage of surgical instruments in an inch-worm-type locomoted endoscopic instrument comprising an extensible tubular central body, wherein said end portions of said tubular member are fixed to the front end and the rear end of said central body, said evenly corrugated intermediate portion axially extending in said central body and being extensible along with it.

6. The tubular guide according to claim 5, wherein the end portion of said tubular member intended for being fixed to the front end of said central body has a flexible and inextensible portion extending in a steering portion of said endoscopic instrument, a further rigid and inextensible portion of said tubular member being provided at the free end of said flexible and inextensible portion fixable to the front end of said steering section.

7. The tubular guide according to claim 1, wherein said elastic element is a coil spring with a circular wire section.

8. The tubular guide according to claim 1, wherein said elastic element is a coil spring with a circular wire section, at one end of which a length of coil spring extends with an axially flattened rectangular or elliptical section.

9. A process for the production of a flexible and extensible tubular guide comprising:
   a tubular member, wherein said tubular member has an intermediate portion which is evenly corrugated in such a way to allow the guide to extend and contract, and
   an elastic element axially arranged in said tubular member and internally to the tubular member,
   said tubular member being further provided with two end portions fixed to said elastic element,
   wherein said evenly corrugated intermediate portion of the tubular member comprises a plurality of mutually interconnected folds forming a plurality of elongated diamond recesses when fully axially compressed, and a plurality of hexagonal recesses when fully axially elongated, and a surface of the tubular member is smoother when the tubular member is fully axially elongated than when the tubular member is fully axially compressed, the process comprising:
   inserting a close-wound spring in a tubular member fit for being plastically deformed;
   firmly securing two end portions of said tubular member to said underlying spring in such a way to cause them to perfectly adhere to said spring;
   firmly locking said end portions and plastically deforming the intermediate portion placed there between by elongating said intermediate portion beyond the elastic deformation threshold of the material, but within the maximum plastic deformation limit; and
   unlocking said end portions to cause the contraction of said intermediate portion and the formation of an even corrugation thereon in the form of folds.

10. The process according to claim 9, wherein said end portions of said tubular member are firmly secured to said spring by sleeves made of heat shrink material which are shrunk around said end portions by thermal treatment.

11. The process according to claim 9, wherein one of said end portions is formed with a flexible and inextensible intermediate portion by plastic deformation following elongation with a elongation ratio such as not to overcome the plastic deformation limit of the material.

12. The process according to claim 9, wherein said tubular member is made of a heat-shrink material.

13. The process according to claim 12, wherein the heat shrink material is a polyolefin material or a polyvinylidene fluoride based material.

14. The process according to claim 9, wherein the elongation ratio of said intermediate portion is 1:5.

15. The process according to claim 9, wherein said spring is a coil spring with a circular section wire and one of its ends consists of a length of coil spring with an axially flattened rectangular or elliptical section.

* * * * *